US009266806B1

(12) United States Patent
Vetter et al.

(10) Patent No.: US 9,266,806 B1
(45) Date of Patent: Feb. 23, 2016

(54) REDUCTIVE CARBONYLATION OF METHANOL TO ACETALDEHYDE

(71) Applicant: Eastman Chemical Company, Kingsport, TN (US)

(72) Inventors: Andrew James Vetter, Kingsport, TN (US); Jonathan Michael Penney, Gray, TN (US); David William Norman, Cary, NC (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/586,070

(22) Filed: Dec. 30, 2014

(51) Int. Cl.
| *C07C 45/49* | (2006.01) |
| *B01J 31/00* | (2006.01) |
| *C07C 45/00* | (2006.01) |
| *B01J 37/04* | (2006.01) |
| *B01J 31/24* | (2006.01) |

(52) U.S. Cl.
CPC ........... *C07C 45/002* (2013.01); *B01J 31/2404* (2013.01); *B01J 37/04* (2013.01); *B01J 2231/44* (2013.01); *B01J 2531/845* (2013.01); *C07C 2523/00* (2013.01); *C07C 2527/16* (2013.01)

(58) Field of Classification Search
CPC .. C07C 45/49; C07C 45/512; B01J 2531/845; B01J 31/0267; B01J 31/0268
USPC .......................... 568/487; 502/162, 164, 169
See application file for complete search history.

(56) References Cited

U.S. PATENT DOCUMENTS

| 2,727,902 | A | 12/1955 | Reppe et al. |
| 4,239,705 | A | 12/1980 | Pretzer et al. |
| 4,293,718 | A | 10/1981 | Gauthier-Lafaye et al. |
| 4,306,091 | A | 12/1981 | Gauthier-Lafaye et al. |
| 4,361,706 | A | 11/1982 | Habib et al. |
| 4,374,285 | A | 2/1983 | Lin et al. |
| 4,374,752 | A * | 2/1983 | Argento et al. ............... 502/162 |
| 4,389,532 | A * | 6/1983 | Larkins et al. ................ 568/487 |
| 4,400,551 | A | 8/1983 | Keim et al. |
| 4,484,002 | A | 11/1984 | Lin |
| 4,556,744 | A | 12/1985 | Griggs et al. |
| 4,954,665 | A | 9/1990 | Vidal |
| 5,770,541 | A | 6/1998 | Vanderspurt et al. |
| 5,908,807 | A | 6/1999 | Vanderspurt et al. |
| 5,939,352 | A | 8/1999 | Vanderspurt et al. |
| 6,034,141 | A | 3/2000 | Vanderspurt et al. |
| 7,700,192 | B2 | 4/2010 | Matthews et al. |
| 7,700,813 | B2 | 4/2010 | Kourtakis et al. |
| 7,745,672 | B2 | 6/2010 | Kourtakis et al. |
| 8,304,587 | B2 | 11/2012 | Warner et al. |
| 2007/0293695 | A1 | 12/2007 | Zoeller et al. |
| 2009/0247783 | A1 | 10/2009 | Zoeller et al. |

FOREIGN PATENT DOCUMENTS

| CN | 101703926 A | 5/2010 |
| DE | 33 43 519 A1 | 6/1985 |
| DE | 35 06 714 A1 | 8/1986 |
| EP | 0 037 586 A1 | 10/1981 |
| FR | 697 726 | 1/1931 |
| FR | 697 727 | 1/1931 |
| FR | 697 896 | 1/1931 |
| JP | 2000 172854 A | 6/2000 |

OTHER PUBLICATIONS

Bahrmann, Helmut; "Homologation—3.2 Special Catalysts and Processes"; Applied Homogeneous Catalysis Organometallic Compounds, vol. 2; pp. 902-914; 1996.
Cuigai, Liu, et al.; "Effect of Double Promoters on $CuO/SiO_2$ Catalyst for Synthesis of Isobutyraldehyde from Methanol and Ethanol"; Petrochemical Technology; pp. 550-553; 2011 (original language and English abstract).
Dinka, P. et al.; "Reaction of methanol and n-propanol over hydrotalcite-like catalysts containing vanadium oxide"; Applied Clay Science, vol. 13; pp. 467-477; 1998.
Gauthier-Lafaye, Jean and Perron, Robert; "Chapter 4 Synthesis of acetaldehyde and ethanol"; methanol and carbonylation; pp. 39-96; 1987.
Gauthier-Lafaye, J. et al.; "Methanol Hydrocarbonylation into Acetaldehyde Catalyzed by Cobalt and Two Different Iodides"; Journal of Molecular Catalysis, vol. 17; pp. 339-347; 1982.
Girard, James W. et al.; "Technical Advantages of Vandium SCR Systems for Diesel NOx Control in Emerging Markets"; SAE Int. J. Fuels Lubr, vol. 1, Issue 1; pp. 488-494; 2008.
Hong, H. et al.; "Study of $V_2 O_5$ Catalyst Deactivation for the Synthesis of Isobutyraldehyde from Methanol and Ethanol"; Chemical Engineering of Oil & Gas, vol. 37, No. 1; pp. 5-8; Feb. 2008 (original language and English abstract).
Hong, H. et al.; "Macrokinetics of Synthesis of Isobutyraldehyde from Methanol and Ethanol over $V_2O_5$ Catalyst"; Chemical Engineering of Oil & Gas, vol. 37, No. 5, pp. 370-372; Oct. 2008 (original language and English abstract).
Keim, W.; "Carbon monoxide: feedstock for chemicals, present and future"; Journal of Organometallic Chemistry, vol. 372; pp. 15-23; 1989.
Loevenich, Heinz and Röper, Michael; "Kinetic Studies of Methanol Homologation Using Cobalt-Phosphine-Iodine Catalysts"; $C_1$ Molecular Chemistry, vol. 1; pp. 155-170; 1984.
Mizoroki, Tsutomu et al.; "Further Study of Methanol Carbonylation Catalyzed by Cobalt, Rhodium, and Iridium Catalysts"; Bulletin of the Chemical Society of Japan, vol. 52, No. 2; pp. 479-482; 1979.
Moloy, Kenneth G. and Wegman, Richard W.; "Rhodium-Catalyzed Reductive Carbonylation of Methanol"; Organometallics, vol. 8; pp. 2883-2892; 1989.
Reddy, B. Mahipal et al.; "A Single-Step Synthesis of Isobutyraldehyde from Methanol and Ethanol over CuO—ZnO—$Al_2O_3$ Catalyst"; Journal Chemical Society, Chemical Commun.; pp. 997-998; 1992.
Reddy, B. M. et al.; "Vapour Phase Synthesis of Isobutyraldehyde from Methanol and Ethanol over Mixed Oxide Supported Vanadium Oxide Catalysts"; Res. Chem. Intermed., vol. 23, No. 8; pp. 703-713; 1997.

(Continued)

*Primary Examiner* — Sikarl Witherspoon
(74) *Attorney, Agent, or Firm* — Jennifer R. Knight

(57) ABSTRACT

Catalyst composition produced by combining a cobalt-containing precursor in an alkyl alcohol with a phosphine ligand to the solution; and subsequently adding an iodine compound. Reductive carbonylation processes using the catalyst composition to produce aldehydes are also provided.

17 Claims, No Drawings

(56) References Cited

OTHER PUBLICATIONS

Sharutin, V. V. et al.; "Synthesis and Structure of Cobalt Complexes [Me$_3$EtN]+$_2$[CoI$_4$]$^{2-}$ and [Me$_3$BuN]+$_2$[CoI$_4$]$^{2-}$"; Russian Journal of Inorganic Chemistry, vol. 56, No. 9; pp. 1384-1389; 2011.

Twigg, Martyn V.; "Progress and future challenges in controlling automotive exhaust gas emissions"; Applied Catalysis B: Environmental, vol. 70; pp. 2-15; 2007.

Wang, Fey-Long and Lin, Yi-Hsuan; "Alkylation of Acetaldehyde with Methanol over Titanium Oxide-Supported Vanadium Oxide"; Chemistry Letters; pp. 1867-1868; 1992.

Wang, Fey-Long, et al.; "Alkylation of aldehydes with methanol over titanium oxide catalysts"; Catalysis Letters, vol. 42; pp. 155-160; 1996.

Wang, Hui-Ying, et al.; "V$_2$O$_5$/TiO$_2$—SiO$_2$ Catalysts for the Synthesis of Isobutyraldehyde from Methanol and Ethanol"; Journal of Shenyang Institute of Chemical Technology, vol. 22, No. 3; pp. 200-203; Sep. 2008 (original language and English abstract).

Wender, Irving et al.; "Ethanol from Methanol"; Science, vol. 113; pp. 206-207; Feb. 23, 1951.

Wegman, Richard W. and Busby, David C.; "The Role of Phosphines and Solvents in CoI$_2$-Catalyzed Reductive Carbonylation of Methanol"; Journal of Molecular Catalysis, vol. 32; pp. 125-136; 1985.

Co-pending U.S. Appl. No. 14/585,884, filed Dec. 30, 2014; Penny et al.

Notice of Allowance dated Jun. 10, 2015 received in U.S. Appl. No. 14/585,884.

Co-pending U.S. Appl. No. 14/585,915, filed Dec. 30, 2014; Vetter et al.

Co-pending U.S. Appl. No. 14/586,094, filed Dec. 30, 2014; Norman et al.

Notice of Allowance dated Jun. 11, 2015 received in U.S. Appl. No. 14/586,094.

Notice of Allowance dated Sep. 18, 2015 received in U.S. Appl. No. 14/586,094.

Co-pending U.S. Appl. No. 14/585,940, filed Dec. 30, 2014; Penny et al.

Non-Final Office Action dated Jun. 9, 2015 received in U.S. Appl. No. 14/585,940.

Notice of Allowance dated Sep. 29, 2015 received in U.S. Appl. No. 14/585,940.

\* cited by examiner

REDUCTIVE CARBONYLATION OF METHANOL TO ACETALDEHYDE

FIELD OF THE INVENTION

This invention relates to a process for the reductive carbonylation of a low molecular weight alcohol to produce the homologous aldehyde. For example, this invention relates to a process for the reductive carbonylation of methanol, hydrogen, and carbon monoxide to form acetaldehyde.

BACKGROUND OF THE INVENTION

Cobalt can catalyze the formation of acetaldehyde from methanol, carbon monoxide, and hydrogen, a reaction known as reductive carbonylation. For example, it was disclosed by Wender et al., *Science*, 113, (1951), 206-207, that a cobalt carbonyl catalyst system could be used. However, the product of the disclosed process was primarily ethanol, together with a small amount of acetaldehyde. It was later shown that the addition of iodide to a cobalt-containing catalyst system increased the amount of acetaldehyde produced. Iodide is typically added as a co-catalyst (also commonly referred to as a promoter) to the reaction in a form such as hydroiodic acid (a strong acid), methyl iodide, elemental iodine, or as an iodide salt such as lithium iodide or sodium iodide.

Homologation of methanol to ethanol can be achieved by addition of a hydrogenation catalyst, typically ruthenium based, to a reductive carbonylation system. For example, Mizoroki, et al., *Bull. Chem. Soc. Japan*, 52, (1979), 479-482, have described a catalyst system containing a cobalt compound, a ruthenium compound and methyl iodide to convert methanol to ethanol with 77% selectivity.

There is, however, a need to influence readily the relative amounts of aldehyde and/or alcohol produced in a reductive carbonylation reaction to maximize the desired product profile. In particular, methods of making aldehydes are desired. There is also a need for an inexpensive catalyst that can be used instead of the typical rhodium catalyst or iridium/ruthenium catalyst for the reductive carbonylation of alcohols.

SUMMARY OF THE INVENTION

The invention provides catalyst compositions, methods of making catalyst compositions, and reductive carbonylation processes that use such catalyst compositions. It has been found that improved performance of such catalysts may be found by controlling the order by which they are combined.

Thus, the invention provides processes for making a catalyst composition, comprising:

a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing wherein the phosphine ligand is of the general formula

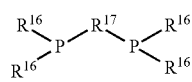

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms.

The invention further provides catalyst compositions produced by a process comprising:

(a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing;

wherein the phosphine ligand is of the general formula

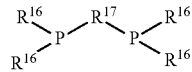

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms.

The invention further provides processes for the preparation of a crude reductive carbonylation product, the process comprising contacting hydrogen, carbon monoxide, and a feed alcohol in the presence of a catalyst composition to form the crude reductive carbonylation product, wherein the crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents, wherein the feed alcohol is selected from methanol, ethanol and n-propanol and wherein the catalyst composition is made by a catalyst preparation process comprising:

a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing; and the phosphine ligand is of the general formula

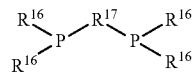

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms.

DETAILED DESCRIPTION

Unless indicated to the contrary, the numerical parameters set forth in the following specification and attached claims can represent approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be from 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention represent approximations, in some cases, the numerical values set forth in the specific examples are intended to be reported precisely in view of methods of measurement. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the denomination of process steps, ingredients, or other aspects of the information disclosed or claimed in the application with letters, numbers, or the like is a convenient means for identifying discrete activities or ingredients and the recited lettering can be arranged in any sequence, unless otherwise indicated or apparent from the context.

As used herein, the singular forms "a", "an", and "the" include plural referents unless the context clearly dictates otherwise. Thus, even use of language such as "at least one" or "at least some" in one location is not intended to imply that other uses of "a", "an", and "the" excludes plural referents unless the context clearly dictates otherwise. Similarly, use of the language such as "at least some" in one location is not intended to imply that the absence of such language in other places implies that "all" is intended, unless the context clearly dictates otherwise.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "alkyl" as used herein refers to a group containing one or more saturated carbons, such as methyl, ethyl, n-propyl, isopropyl, n-butyl, iso-butyl, tert-butyl and the like.

The term "crude reductive carbonylation product", as used herein, refers to the reaction products of carbon monoxide and an alcohol, and hydrogen. The crude reductive carbonylation product comprises the many different compounds produced under reductive carbonylation conditions. The crude reductive carbonylation product is the liquid effluent directly exiting the carbonylation reactor, before any separation of the homogeneous catalyst or other liquid compounds. The crude reductive carbonylation product comprises the homologous aldehyde, homologous acid, and/or homologous alcohol, unreacted feed, and other byproducts, as well as the catalyst.

The term "catalyst", as used herein, has its typical meaning to one skilled in the art as a substance that increases the rate of chemical reactions without being consumed. The term "catalyst composition", as used herein refers to a catalyst comprising multiple components, such as a composition that contains both a product of contacting a cobalt-containing precursor with a phosphine ligand and an iodine compound promoter.

The term "phosphine ligand", as used herein, refers to an organic compound composed of hydrocarbyl groups covalently bound to one or more phosphorus atoms in the +3 oxidation state. Such phosphine ligands are commonly referred to as tertiary phosphine since the phosphorus atom is substituted by three groups.

Describing two phosphorus atoms as "bridged by" a number of carbon atoms, as used herein, refers to the smallest number of consecutive atoms in a path between two atoms, specifically the two phosphorus atoms. For example, 1,3-bis (diphenyl phosphino)propane is bridged by 3 carbon atoms, 1,4-bis(diphenyl phosphino) butane is bridged by 4 carbon atoms, 1,2-bis(diphenylphosphino)benzene is bridged by 2 carbon atoms, bis(diphenylphosphinomethyl)biphenyl is bridged by 6 carbon atoms, and 1,1,1-tris(diphenylphosphinomethyl)ethane is bridged by 3 carbon atoms.

The term "alkylene", as used herein, refers to an alkylene-diyl group having free valences at each group end to bond to the two phosphorus atoms. The terms "cycloalkylene", "arylene", and "biarylene" are used in a like manner. When the term "substituted or unsubstituted" is followed by a listing of hydrocarbon groups or other groups, the term is intended to modify each group. When a listing of hydrocarbon groups is followed by the term, "each having up to [a number of] carbon atoms", the term is intended to modify each group. The term "substituted", as used herein, has its usual meaning in the art, as in the hydrogen on the hydrocarbon may be substituted with the stated group. The term "heteroatom", as used herein has its usual meaning in the art, as an atom, such as nitrogen, oxygen, sulfur, or phosphorus, substituted for a carbon atom in a hydrocarbon.

The term "homologous aldehyde", as used herein, refers to an aldehyde containing one more carbon atom than the alcohol used to produce it. For example, n-propionaldehyde is the homologous aldehyde of ethanol reductive carbonylation.

The term "homologous aldehyde equivalents", as used herein refers to the common products and byproducts containing at least one aldehyde group. The specific homologous aldehyde equivalents for methanol, ethanol, and propanol reductive carbonylation are given in the specification.

The term "homologous acid", as used herein, refers to an acid containing one more carbon atom than the alcohol used to produce it. For example, n-propionic acid is the homologous acid of ethanol reductive carbonylation. The term "homologous acid equivalents", as used herein refers to the common products and byproducts containing at least one acid group. The specific homologous acid equivalents for methanol, ethanol, and propanol reductive carbonylation are given in the specification.

The term "homologous alcohol", as used herein, refers to an alcohol containing one more carbon atom than the alcohol used to produce it. For example, n-propanol is the homologous alcohol of ethanol reductive carbonylation. The term "homologous alcohol equivalents", as used herein refers to the common products and byproducts containing at least one alcohol group. The specific homologous alcohol equivalents for methanol, ethanol, and propanol reductive carbonylation are given in the specification.

The term "higher mole percent" as used herein, refers to a larger number of moles of one component than another component in a mixture. For example, if a crude reductive carbonylation product contains 60 mole percent acetaldehyde equivalents, 30 mole percent acetic acid equivalents, and 10 mole percent ethanol equivalents, on a total acetaldehyde equivalents, acetic acid equivalents, and ethanol equivalents basis, then the crude reductive carbonylation product has a higher mole percent of acetaldehyde equivalents than either of acetic acid equivalents or ethanol equivalents. In the specific example, the crude reductive carbonylation product has 60−30=30 mole percent higher acetaldehyde equivalents than acetic acid equivalents and 60−10=50 mole percent higher acetaldehyde equivalents than ethanol equivalents.

The term "reductive carbonylation conditions" means any combination of temperature, pressure and constituents under which reductive carbonylation of a primary alcohol having one to three carbons will occur in the presence of sufficient quantities amounts and proportions of catalyst, alkyl iodide, carbon monoxide, hydrogen and alcohol (without the presence of catalyst poisons or other components that may prevent reductive carbonylation from occurring). "Reductive carbonylation" means the reaction of an alkyl alcohol having n carbons with hydrogen and carbon monoxide in the presence of a sufficient concentration of hydrogen to result in reaction products that include an aldehyde having n+1 carbons, an alkyl alcohol having n+1 carbons, or a combination of the two and the sum of the mole percent of aldehydes having n+1 carbons in the reaction product and the mole percent of alcohols having n+1 carbons in the reaction product is greater than the mole percent of carboxylic acids having n+1 carbons in the reaction product.

The term "precursor cobalt equivalents" shall mean the product of multiplying the number of moles of a cobalt-containing precursor by the number of cobalt atoms in the molecular formula of the cobalt compound. Thus, four moles of a promoter whose molecular formula includes four cobalt atoms (e.g. tetracobalt dodecacarbonyl) contains 4×4=16 precursor cobalt equivalents while four moles of cobalt (II) iodide has 4×1=4 precursor cobalt equivalents.

The term "promoter iodine equivalents" means the product of multiplying the number of moles of iodine compound in a promoter by the number of iodine atoms in the molecular formula of the iodine compound. Thus four moles of elemental iodine ($I_2$) promoter has 4×2=8 promoter iodine equivalents while four moles of methyl iodide (MeI) promoter has 4×1=4 promoter iodine equivalents.

The invention provides catalyst compositions, processes for making catalyst compositions, and reductive carbonylation processes that use the catalysts of the invention. The catalyst compositions of the present invention can be used, for example, in the reductive carbonylation of methanol to acetaldehyde. The catalyst compositions can be prepared with a cobalt-containing precursor, a phosphine ligand, and a promoter comprising an iodine compound. It has been found, however, that catalyst composition performance is improved if the cobalt-containing precursor and the phosphine ligand are contacted in a liquid composition prior to combining them with the iodine compound.

The invention thus provides a process for making a catalyst composition, wherein the process comprises:

(a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine ("I2" or "$I_2$"), compounds that will form an alkyl iodide, hydroiodic acid, an alkali metal iodide or elemental iodine under reductive carbonylation conditions or combinations of two or more of the foregoing wherein the phosphine ligand is of the general formula;

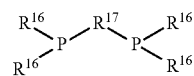

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms.

The invention further provides catalyst compositions made according to a process comprising:

(a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing;

wherein the phosphine ligand is of the general formula

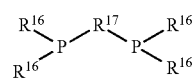

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms.

The cobalt-containing precursor in the catalysts as well as the methods for making them can be any cobalt compound that will adequately dissolve with the carrier liquid to allow it to contact and interact with the ligand while the cobalt compound and ligand are together in the carrier liquid. In one embodiment, the cobalt-containing precursor is selected from cobalt halides, cobalt carbonyls, and cobalt containing organic ligands. Some examples of cobalt halides include cobalt(II) chloride, cobalt(II) bromide and cobalt(II) iodide. Some examples of cobalt containing organic ligands include, cobalt(II) acetylacetonate, cobalt(II) citrate and cobalt(II) bis(stearate). Some examples of cobalt carbonyls include dicobalt octacarbonyl and tetracobalt dodecacarbonyl. In one embodiment, the cobalt-containing precursor is selected from cobalt iodide, dicobalt octacarbonyl, and tetracobalt dodecacarbonyl. In one embodiment, the cobalt-containing precursor is selected from cobalt iodide and dicobalt octacarbonyl. In one embodiment, the cobalt-containing precursor is cobalt iodide.

The phosphine ligand in the catalysts as well as the methods for making them is a multidentate compound containing at least two bridged phosphorus atoms. The phosphine ligand can be of the general formula

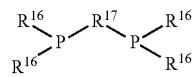

The phosphorus atoms P are bridged by 2 or 3 atoms of $R^{17}$. $R^{17}$ can be a substituted or unsubstituted alkylene, cycloalkylene, arylene and/or biarylene, each having up to 22 carbon atoms. $R^{17}$ can optionally contain one or more heteroatoms. The heteroatom can be nitrogen, oxygen, sulfur, phosphorus, or mixtures thereof. $R^{16}$ is a substituted or unsubstituted alkyl, alkoxy, cycloalkyl, aryl, and/or aryloxy, each having up to 20 carbon atoms.

The phosphorus atoms P are bridged by 2 or 3 atoms which means that the shortest molecular path between the two phosphorus atoms contains 2 or 3 atoms. These 2 or 3 atoms are referred to as bridging atoms. The bridging atoms can be carbon and/or a heteroatom selected from nitrogen, oxygen, sulfur, phosphorus or mixtures thereof.

In one aspect, $R^{17}$ can be a straight- or branch-chain hydrocarbon radical containing 2 or 3 bridging atoms, where the bridging atoms can be substituted, for example, with alkyl, alkoxy, aryl, dialkylphosphinomethyl, diarylphosphino, or diarylphosphinomethyl.

In another aspect, $R^{17}$ can be arylene or biarylene. The arylene or biarylene can be substituted, for example, with methyl, ethyl, propyl, iso-propyl, butyl, iso-butyl, methoxy, ethoxy, propoxy, iso-propoxy, butoxy, iso-butoxy, phenoxy, nitro, chloro, fluoro, trifluoromethyl. In another aspect, the arylene or biarylene can be substituted with methyl, ethyl, propyl, or iso-propyl.

In one aspect, $R^{16}$ can be a substituted alkyl, alkoxy, cycloalkyl, aryl, or aryloxy wherein the substituted group can be, for example, methyl, ethyl, propyl, iso-propyl, butyl, iso-butyl, methoxy, ethoxy, propoxy, iso-propoxy, butoxy, iso-butoxy, phenoxy, nitro, chloro, fluoro, or trifluoromethyl. In another aspect, the substituted group can be methyl, ethyl, propyl, or iso-propyl.

In one aspect, $R^{16}$ is chosen from phenyl, naphthyl, anthryl, tetrahydronaphthyl, or octahydronaphthyl each of which can be substituted with alkyl, alkoxy, aryl, aryloxy, halogen, or nitro. In one aspect, $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy.

Without representing an exhaustive list, specific examples of multidentate phosphine ligands useful in the present invention include 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino)propane; 2,4-bis(dicyclohexylphosphino)pentane; 1,2-bis(dimethylphosphino)ethane; 1,3-bis(dimethylphosphino)propane; 2,4-bis(dimethylphosphino)pentane; 1,2-bis(diisopropylphosphino)ethane; 1,3-bis(diisopropylphosphino)propane; 2,4-bis(diisopropylphosphino)pentane; 1,2-bis(di-tert-butylphosphino)ethane; 1,3-bis(di-tert-butylphosphino)propane; 2,4-bis(di-tert-butylphosphino)pentane; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; 1,3-bis(diphenylphosphino)cyclobutane; 1,2-bis(diphenylphosphino)cyclohexane; 1,2-bis(diphenylphosphino)cyclopentane; 1,2-bis(diphenylphosphino)cyclobutane; and/or 1,2-bis(diphenylphosphino)cyclopropane.

In one aspect the phosphine ligand can be chosen from 1,2-bis(diphenylphosphino)ethane; 1,2-bis(diphenylphosphino)benzene; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect, the phosphine ligand can be chosen from 1,3-bis(diphenylphosphino)propane; 1,1,1,-tris(diphenylphosphinomethyl)ethane; 1,1,1-tris(diethylphosphinomethyl)ethane; p 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect the phosphine ligand can be 1,2-bis(diphenylphosphino)ethane; 1,2-bis(diphenylphosphino)benzene; 1,3-bis(diphenylphosphino)propane; and/or 1,1,1-tris(diphenylphosphinomethyl)ethane. In one aspect, the phosphine ligand can be 1,3-bis(diphenylphosphino)propane, 1,1,1,-tris (diphenylphosphinomethyl)ethane; and/or 1,1,1-tris(diethylphosphinomethyl)ethane.

In one aspect, the phosphorus atoms are bridged by saturated or unsaturated alkylene containing three carbon atoms. The phosphine ligand can be of the general formula

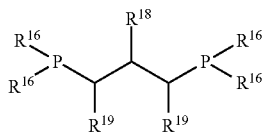

In one aspect, $R^{18}$ can be a hydrogen radical or a hydrocarbon radical having up to 17 carbon atoms. The hydrocarbon radical can be substituted with alkyl, alkoxy, cycloalkyl aryl, aryloxy dialkylphosphinomethyl, diarylphosphinomethyl, or mixtures thereof. In another aspect, $R^{18}$ can be a hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butylphosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosphinomethyl, di-iso-butoxyphosphinomethyl, di-tert-butoxyphosphinomethyl diphenylphosphinomethyl, ditolylphosphinomethyl, or dixylylphosphinomethyl.

$R^{19}$ can be a hydrogen radical or a substituted or unsubstituted alkyl, alkoxy, cycloalkyl, aryl, and aryloxy, each having up to 8 carbon atoms. In one aspect, $R^{19}$ can be a hydrogen radical or a substituted or unsubstituted alkyl. In one aspect, $R^{19}$ can be a hydrogen radical.

In one aspect $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy.

In one aspect, $R^{16}$ or $R^{18}$ can be unsubstituted aryl, alkyl, cycloalkyl, alkoxy, or aryloxy substituted, for example, with groups selected from methyl, ethyl, propyl, iso-propyl, butyl, iso-butyl, methoxy, ethoxy, propoxy, iso-propoxy, butoxy, iso-butoxy, phenoxy, nitro, chloro, fluoro, and/or trifluoromethyl.

In one aspect, $R^{16}$ or $R^{18}$ can be aryl groups chosen from phenyl, naphthyl, anthryl, tetrahydronaphthyl, and/or octahydronaphthyl with any of the groups substituted with alkyl, alkoxy, aryl, aryloxy, halogen, and/or nitro.

In one aspect, the phosphorus atoms are bridged by saturated or unsaturated alkylene containing three carbon atoms. The phosphine ligand can be of the general formula

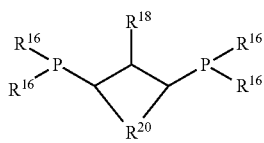

$R^{20}$ can be a substituted or unsubstituted alkyl having up to 8 carbon atoms, forming a cycloalkyl group between the phosphorus atoms. $R^{18}$ is a hydrogen radical and $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy.

The promoter comprises an iodine compound. In one aspect, the iodine compound is selected from alkyl iodides, hydroiodic acid, alkali metal iodides, elemental iodine ("iodine," "I2" or "$I_2$"), compounds that will form an alkyl iodide, hydroiodic acid, an alkali metal iodide or elemental iodine under reductive carbonylation conditions or combinations of two or more of the foregoing. In one embodiment, the compound that will form an alkyl iodide, hydroiodic acid, alkali metal iodides or elemental iodine under reductive carbonylation conditions comprises a compound selected from alkyl and aryl iodides having from 1 to 12 carbon atoms such as methyl iodide, ethyl iodide, 1-iodopropane, 2-iodobutane, 1-iodobutane, and benzyl iodide. In one embodiment, the compound that will form an alkyl iodide, hydroiodic acid, an alkali metal iodide or elemental iodine under reductive carbonylation conditions comprises a compound selected from alkyl halides having 1 to 6 carbon atoms. Some examples of alkali metal iodides include lithium iodide, sodium iodide, potassium iodide and rubidium iodide. In one embodiment, the iodine compound is selected from lithium iodide, hydroiodic acid, sodium iodide, methyl iodide, ethyl iodide and elemental iodine. In one embodiment, the iodine compound is selected from lithium iodide, methyl iodide and elemental iodine. In one embodiment, the iodine compound is methyl iodide.

In one embodiment of either the catalyst or the method for making above, the cobalt precursor is selected from cobalt iodide, dicobalt octacarbonyl and tetracobalt dodecacarbonyl, the promoter is selected from lithium iodide, sodium iodide, hydroiodic acid, methyl iodide and elemental iodine, and the phosphine ligand is selected from 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino) propane; 2,4-bis(dicyclohexylphosphino)pentane; 1,2-bis (dimethylphosphino)ethane; 1,3-bis(dimethylphosphino) propane; 2,4-bis(dimethylphosphino)pentane; 1,2-bis (diisopropylphosphino)ethane; 1,3-bis (diisopropylphosphino)propane; 2,4-bis (diisopropylphosphino)pentane; 1,2-bis(di-tert-butylphosphino)ethane; 1,3-bis(di-tert-butylphosphino) propane; 2,4-bis(di-tert-butylphosphino)pentane; 2,2'-bis (diphenylphosphino)-1,1'-biphenyl; (2-butoxy-2-((diphenylphosphino)methyl)propane-1,3-diyl)bis (diphenylphosphine); 1,8-bis(diphenylphosphino) naphthalene; bicyclo[2.2.1]heptane-2,7-diylbis (diphenylphosphine); 1,3-bis(diphenylphosphino) cyclohexane; 1,3-bis(diphenylphosphino)cyclopentane; 1,3-bis(diphenylphosphino)cyclobutane; 1,2-bis (diphenylphosphino)cyclohexane; 1,2-bis (diphenylphosphino)cyclopentane; 1,2-bis (diphenylphosphino)cyclobutane; and/or 1,2-bis (diphenylphosphino)cyclopropane.

In embodiment of either the catalyst or the method for making above, the cobalt precursor is selected from cobalt iodide and dicobalt octacarbonyl and tetracobalt dodecacarbonyl, the promoter is selected from methyl iodide, lithium iodide; hydroiodic acid and elemental iodine, and the phosphine ligand is selected from 1,3-bis(diphenylphosphino)

propane, 1,2-bis(diphenylphosphino)ethane, 1,2-bis(diphenylphosphino)benzene, and 1,1,1-tris(diphenylphosphinomethyl)ethane.

In embodiment of either the catalyst or the method for making above, the cobalt precursor is cobalt(II) iodide, the iodine compound is selected from at least one of the group consisting of iodine, methyl iodide, and lithium iodide, and the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphino-methyl)ethane.

In one embodiment of either the catalyst or the method for making above, the cobalt precursor is cobalt(II) iodide, the iodine compound is methyl iodide, and the phosphine ligand is 1,3-bis(diphenylphosphino)propane.

The catalyst is made using a liquid composition comprising a product of contacting a cobalt-containing precursor with a phosphine ligand in the presence of a carrier liquid. As used herein, "carrier liquid" shall mean any compound, composition or combination thereof that is a liquid having a dielectric constant of at least 2.0 at 20° C. The constituents of the carrier liquid should not include unacceptably high concentrations of compounds whose structural, electronic or other characteristics would unacceptably interfere with the interaction between cobalt and the phosphine ligand (for example, by irreversibly complexing with the cobalt or the phosphine in a way that would interfere with the interaction). The carrier can be selected from liquids having a dielectric constant of at least 3.0, at least 4.0, at least 5.0, at least 7.5, at least 10.0, at least 12.5, at least 15.0, at least 17.5, at least 30.0, or at least 35, in all cases at 20° C. Alternately, the carrier can be selected from liquids having a dielectric constant of 2.0 to 90.0, 5.0 to 90.0, 10.0 to 90.0, 15.0 to 90.0, 20.0 to 90.0, 25.0 to 90.0, 30.0 to 90.0, 35.0 to 90.0, 40.0 to 90.0, 2.0 to 80.0, 5.0 to 80.0, 10.0 to 80.0, 15.0 to 80.0, 20.0 to 80.0, 25.0 to 80.0, 30.0 to 80.0, 35.0 to 80.0, 40.0 to 80.0, 2.0 to 70.0, 5.0 to 70.0, 10.0 to 70.0, 15.0 to 70.0, 20.0 to 70.0, 25.0 to 70.0, 30.0 to 70.0, 35.0 to 70.0, 40.0 to 70.0, 2.0 to 60.0, 5.0 to 90.0, 10.0 to 60.0, 15.0 to 60.0, 20.0 to 60.0, 25.0 to 60.0, 30.0 to 60.0, 35.0 to 60.0, 40.0 to 60.0, 2.0 to 50.0, 5.0 to 50.0, 10.0 to 50.0, 15.0 to 50.0, 20.0 to 50.0, 25.0 to 50.0, 30.0 to 50.0, 35.0 to 50.0 or 40.0 to 50.0, in all cases at 20° C. Some examples of carrier liquids include compounds selected from ketones having 5 to 20 carbon atoms, alcohols having 1 to 20 carbons, aryl compounds and alkylaryl compounds having 7 to 20 carbon atoms, ethers having 2 to 20 carbon atoms, alkyl carbonate esters having from 3 to 20 carbon atoms, carboxylic acid esters having 2 to 20 carbon atoms, carboxylic acids having 1 to 20 carbon atoms and combinations of two or more of the foregoing. In one embodiment, the carrier liquid comprises a compound selected from benzene, toluene, xylenes, methyl napththalenes, 3-methyl-2-butanone, methyl isobutyl ketone (also known as 4-methyl-2-pentanone), methyl isopropyl ketone, methyl propyl ketone, diisobutyl ketone, methanol, ethanol, propanol, iso-propanol, iso-butanol, n-butanol, diisopropylether, dibutylether, diethyl ether, tertiary-amyl methyl ether, tertiary-butyl methyl ether, isobutylisobutyrate, dimethyl carbonate, diethyl carbonate, dipropyl carbonate, diphenyl carbonate, methyl acetate, ethyl acetate, n-butyl acetate, isobutylacetate, isopropylacetate, n-propyl acetate, acetic acid, propionic acid, butyric acid, iso-butyric acid, valeric acid and combinations of two or more of the foregoing. In one embodiment, the carrier liquid comprises a compound selected from methanol, methyl acetate, acetic acid, ethanol, ethyl acetate, propionic acid and combinations of two or more of the foregoing. In one embodiment, the carrier liquid comprises a compound selected from methanol, acetic acid, methyl acetate, and combinations of two or more of the foregoing. In one embodiment, the carrier liquid comprises a compound selected from ethanol, propionic acid, ethyl acetate, and combinations of two or more of the foregoing. In one embodiment, the carrier liquid comprises a compound selected from n-propanol, butanoic acid, propyl acetate, and combinations of two or more of the foregoing. In one embodiment, the carrier liquid comprises methanol.

Combining the cobalt-containing precursor with a phosphine ligand in the presence of the carrier liquid can be carried out by any effective process. For example, the cobalt-containing precursor can be first combined with the carrier liquid, and the resulting combination is then combined with the phosphine ligand. As another example, the phosphine ligand can be first combined with carrier liquid and the resulting combination can be then combined with the cobalt-containing precursor. Optionally, there may be a delay between the first and second combining steps. For example, a delay may be desirable to allow for adequate mixing or other equilibration. This delay may optionally occur for any desired period, such as at least 5 minutes, at least 10 minutes, at least 30 minutes, at least 60 minutes, at least two hours, at least five hours, at least 10 hours, at least 15 hours, at least 24 hours or at least 48 hours. As yet another example, the phosphine ligand and cobalt-containing precursor can each be combined with separate aliquots of carrier liquid and the two aliquots can then be combined. The phosphine ligand and cobalt-containing precursor can also be combined with the carrier liquid simultaneously.

In one embodiment, the liquid composition that is combined with the promoter contains the carrier liquid. This is the case, for example, when the composition that results from combining the phosphine ligand, the cobalt-containing precursor and carrier liquid is then used as the liquid composition and combined with the promoter without further processing. However, the invention also includes embodiments in which the composition that results from combining the phosphine ligand, the cobalt-containing precursor and carrier liquid is processed further. Such further processing can include, for example, adding components, removing components or both. For example, the product that results from contacting the cobalt-containing precursor with the phosphine ligand may be separated from some or all of the carrier liquid and concentrated into a different liquid, for example using techniques such as extraction, distillation, membrane separation or combinations thereof. This may be useful if the carrier liquid is suitable for contacting the cobalt-containing precursor with the phosphine ligand but less desirable for contacting the resulting contact product with the promoter.

The liquid composition is then combined with the promoter to provide the catalyst composition. Optionally, there may be a delay between making the liquid composition and combining it with the promoter. For example, in some cases combining the phosphine ligand and the cobalt precursor causes visible changes in the liquid composition such as formation of particles, color change or both. While not wanting to be bound to a particular theory, such visible effects may be due to a complexation or other interaction between the phosphine ligand and cobalt precursor. Thus, in such cases it may be desirable to allow passage of time after combining the phosphine ligand and cobalt precursor before adding the promoter to allow any such interaction to occur. The period of time may be marked by the completion of a visible change, for example. Alternatively, the delay may optionally occur for any desired period, such as at least 5 minutes, at least 10 minutes, at least 30 minutes, at least 60 minutes, at least two hours, at least five hours, at least 10 hours, at least 15 hours, at least 24 hours, or at least 48 hours.

The liquid composition and the promoter may be combined by any suitable process. For example, either or both of the liquid composition and the promoter may or may not be combined with other constituents prior to the combination of the two.

Neither temperature nor pressure is critical to the process for making the catalyst and any suitable pressure and temperature can be used. For example, the catalyst may be prepared at ambient temperature and pressure or at temperature above or below ambient temperature as well as pressures above or below ambient pressure as is convenient and suitable to the process, (e.g., by avoiding extreme temperatures that may cause decomposition of components of the catalyst or extreme pressures that may interfere with the interaction between the phosphine ligand and the cobalt-containing precursor).

In one aspect of the invention, the molar ratio of the phosphine ligand to the precursor cobalt equivalents (phosphine ligand:precursor Co) used in making the catalyst ranges from 0.01:1 to 2:1. In other examples, the molar ratio of phosphine ligand to the precursor cobalt equivalents (phosphine ligand: precursor Co) ranges from 0.025:1 to 2:1, from 0.025:1 to 0.5, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10 or from 2:1 to 1:5.

In one aspect of the invention, the molar ratio of the phosphine ligand to the promoter iodine equivalents (ligand:promoter iodine) used in making the catalyst ranges from 100:1 to 1:100, from 0.025:1 to 2:1, from 0.025:1 to 0.5, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10, from 2:1 to 1:5, from 10:1 to 1:50, from 5:1 to 1:10, from 0.025:1 to 2:1, from 0.025:1 to 0.5:1, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10, or from 1:1 to 1:3.

In one aspect of the invention, the molar ratio of the promoter iodine equivalents to precursor cobalt equivalents (promoter iodine:precursor Co) ranges from 100:1 to 1:10. In other examples, the molar ratio of ranges from 0.025:1 to 2:1, from 0.025:1 to 0.5:1, from 0.025:1 to 1:1, from 0.025:1 to 1.5:1, from 0.1:1 to 1:1, from 0.1:1 to 0.1:1.5, from 1:1 to 2:1, from 50:1 to 1:10, from 10:1 to 1:2, from 20:1 to 1:1, from 10:1 to 1:3, from 5:1 to 1:1, from 100:1 to 1:10, from 50:1 to 1:1, from 10:1 to 1:1, or from 3:1 to 1:1. For a catalyst composition, the measurement of the above ratios may be made by determining the amounts present in a given volume of the catalyst composition.

In one embodiment, the product of contacting the liquid composition with the promoter is the catalyst composition of the invention. However, the product of contacting the liquid composition with the promoter may also be processed further to result in the reductive carbonylation catalyst. Such further processing can include, for example, adding components, removing components or both. For example, the product of contacting the liquid composition with the promoter may optionally be separated from some or all of the liquid components of the liquid composition, for example using techniques such as extraction, distillation, membrane separation or combinations thereof. This may be useful, for example, if the liquid composition includes components that are suitable for contacting the liquid composition with the promoter but less desirable for use as a reductive carbonylation catalyst.

It will thus be understood that the resulting catalyst composition may or may not contain the carrier liquid. As explained above, the carrier liquid may or may not be present in the liquid composition when it is combined with the promoter. Similarly, the carrier liquid may or may not be present in the reductive carbonylation catalyst.

The catalyst composition of the invention can be used in a process for the reductive carbonylation of a low molecular weight alcohol to its homologous aldehyde or alcohol. Thus, another embodiment for the invention is a process comprising contacting hydrogen, carbon monoxide, and a feed alcohol in the presence of a catalyst composition to form a crude reductive carbonylation product, wherein the crude reductive carbonylation product comprises acetaldehyde equivalents in a higher mole percent than acetic acid equivalents or ethanol equivalents, (each based on the total moles of the acetaldehyde equivalents, the acetic acid equivalents, and the ethanol equivalents), wherein the feed alcohol is selected from methanol, ethanol and n-propanol and wherein the catalyst composition is made by a process comprising:

a) providing a liquid composition comprising a product of contacting a cobalt-containing precursor with a phosphine ligand in the presence of a carrier liquid;

(b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing; and the phosphine ligand is of the general formula

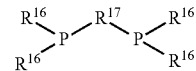

wherein phosphorus atoms P are bridged by 2 or 3 atoms of $R^{17}$, wherein $R^{17}$ is selected from at least one of the group consisting of substituted or unsubstituted alkylene, cycloalkylene, arylene, and biarylene, each having up to 22 carbon atoms, and wherein a heteroatom optionally can substitute for one or more of the carbon atoms, the heteroatom being selected from at least one of the group consisting of nitrogen, oxygen, sulfur, and phosphorus, and $R^{16}$ is selected from at least one of the group consisting of substituted or unsubstituted alkyl, alkoxy, cycloalkyl, aryl, and aryloxy, each having up to 20 carbon atoms. In one embodiment, the feed alcohol is selected from methanol and ethanol. In one embodiment, the feed alcohol is selected from methanol and n-propanol. In one embodiment, the feed alcohol is methanol.

It is understood that the descriptions hereinabove regarding the catalyst composition, the cobalt-containing precursor, the phosphine ligands, the promoters, and the molar ratio of phosphine ligand to cobalt, and all embodiments, ranges and combinations thereof described above, apply equally well to each embodiment of the process comprising contacting hydrogen, carbon monoxide, and a feed alcohol in the presence of a catalyst composition to form the crude reductive carbonylation product.

In one aspect, the amount of methyl iodide present in the crude reductive carbonylation product is less than that in other methanol carbonylation processes. In one aspect, crude reductive carbonylation product t comprises less than 1 weight percent methyl iodide, based on the total weight of the crude reductive carbonylation product. In other aspects, the crude reductive carbonylation product comprises less than 0.8 weight percent, less than 0.5 weight percent, less than 0.1 weight percent, less than 0.05 weight percent, less than 100 ppm, less than 50 ppm, less than 10 ppm, less than 100 ppb, less than 50 ppb, or less than 10 ppb of methyl iodide, based on the total weight of the crude reductive carbonylation product.

In one aspect, the crude reductive carbonylation product comprises homologous aldehyde equivalents in a higher mole percent than homologous acid equivalents or homologous alcohol equivalents from the reaction of carbon monoxide, hydrogen, and the alcohol. In one aspect the alcohol comprises methanol and the crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents. In one aspect, the alcohol comprises ethanol and the crude reductive carbonylation product comprises n-propionaldehyde equivalents in a higher mole percent than n-propionic acid equivalents or n-propanol equivalents, each based on the total moles of n-propionaldehyde equivalents, n-propionic acid equivalents, and n-propanol equivalents. In one aspect, the alcohol comprises n-propanol and the crude reductive carbonylation product comprises n-butyraldehyde equivalents in a higher mole percent than n-butyric acid equivalents, or n-butanol equivalents, each based on the total moles of n-butyraldehyde equivalents, n-butyric acid equivalents, and n-butanol equivalents.

The total moles of homologous aldehyde equivalents are determined as the sum of the moles of reductive carbonylation product compounds that have at least one aldehyde group, with the number of moles of each compound multiplied by the number of aldehyde groups in the compound. For example, when methanol is reductively carbonylated, the homologous aldehyde equivalents are the sum of the moles Acetaldehyde+3*moles Paraldehyde+moles Acetaldehyde dimethyl acetal+moles Acetaldehyde methyl ethyl acetal+moles Acetaldehyde diethyl acetal. The total moles of homologous acid equivalents and homologous alcohol equivalents are determined in the same manner. The homologous aldehyde equivalents, homologous acid equivalents, and homologous alcohol equivalents for methanol, ethanol, and n-propanol reductive carbonylation are listed below.

For methanol reductive carbonylation, homologous aldehyde equivalents, homologous acid equivalents, and homologous alcohol equivalents—acetaldehyde equivalents, acetic acid equivalents, and ethanol equivalents—are given below.

| Acetaldehyde Equivalents | Acetic Acid Equivalents | Ethanol Equivalents |
|---|---|---|
| Acetaldehyde | Acetic acid | Ethanol |
| Acetaldehyde dimethyl acetal | Methyl acetate | Acetaldehyde diethyl acetal |
| Acetaldehyde methyl ethyl acetal | Ethyl acetate | Acetaldehyde methyl ethyl acetal |
| Acetaldehyde diethyl acetal |  | Diethyl ether |
| Paraldehyde |  | Methyl ethyl ether |
|  |  | Ethyl acetate |

For ethanol reductive carbonylation, homologous aldehyde equivalents, homologous acid equivalents, and homologous alcohol equivalents—n-propionaldehyde equivalents, n-propionic acid equivalents, and n-propanol equivalents—are given below.

| Propionaldehyde Equivalents | Propionic Acid Equivalents | Propanol Equivalents |
|---|---|---|
| Propionaldehyde | Propionic acid | 1-Propanol |
| Propionaldehyde diethyl acetal | Ethyl propionate | Propionaldehyde di-n-propyl acetal |
| Propionaldehyde n-propyl ethyl acetal | Propyl propionate | Propionaldehyde n-propyl ethyl acetal |
| Propionaldehyde di-n-propyl acetal |  | Di-n-propyl ether |
| 2,4,6-triethyl-1,3,5-trioxane |  | n-Propyl ethyl ether |
|  |  | n-Propyl propionate |

For n-propanol reductive carbonylation, homologous aldehyde equivalents, homologous acid equivalents, and homologous alcohol equivalents—n-butyraldehyde equivalents, n-butyric acid equivalents, and n-butanol equivalents—are given below.

| Butyraldehyde Equivalents | Butyric Acid Equivalents | Butanol Equivalents |
|---|---|---|
| n-Butyraldehyde | n-Butyric acid | 1-Butanol |
| n-Butyraldehyde di-n-propyl acetal | n-Propyl butyrate | n-Butyraldehyde di-n-butyl acetal |
| n-Butyraldehyde n-butyl n-propyl acetal | n-Butyl butyrate | n-Butyraldehyde n-butyl n-propyl acetal |
| n-Butyraldehyde di-n-butyl acetal |  | Di-n-butyl ether |
| 2,4,6-tripropyl-1,3,5-trioxane |  | n-Butyl n-propyl ether |
|  |  | n-Butyl butyrate |

The hydrogen and carbon monoxide contacted with an alcohol can be obtained from typical sources that are well known in the art. For example, the carbon monoxide and hydrogen can be provided by any of a number of methods known in the art including steam or carbon dioxide reforming of carbonaceous materials such as natural gas or petroleum derivatives; partial oxidation or gasification of carbonaceous materials, residuum, bituminous, sub bituminous, and anthracitic coals and cokes; lignite; oil shale; oil sands; peat; biomass; petroleum refining residues of cokes; and the like. For example, the carbon monoxide can be provided to the reaction mixture as a component of synthesis gas or "syngas", comprising carbon dioxide, carbon monoxide, and hydrogen. The hydrogen and carbon monoxide can be mixed together before the contacting, or a stream of hydrogen and a separate stream of carbon monoxide can be contacted with the alcohol.

The molar ratio of carbon monoxide to hydrogen ($CO:H_2$) can vary over a wide range. For example, $CO:H_2$, can range from 50:1 to 1:50. In other examples, $CO:H_2$ ranges from 10:1 to 1:10 or 5:1 to 1:5 or 3:1 to 1:3 or 2:1 to 1:2 or 10:1 to 1:1 or 5:1 to 1:1 or 2:1 to 1:1 or 2:1 to 1:5 or 1:1 to 1:5 or 1:1 to 1:10.

Each of the above processes described above can be conducted under continuous, semi-continuous, and batch modes of operation and can utilize a variety of reactor types. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, equipment maintenance, or scheduled shut down periods. The term "batch" process as used herein means a process wherein all the reactants are added to the reaction zone and then processed according to a predetermined course of reaction during which no material is fed or removed into the reactor. The term "semicontinuous" means a process where some of the reactants are charged at the beginning of the process and the remaining reactants are fed continuously as the reaction progresses to completion. Alternatively, a semicontinuous process may also include a process similar to a batch process in which all the reactants are added at the beginning of the process except that one or more of the products are removed continuously as the reaction progresses.

Any effective reactor designs or configurations may be used in carrying out either the reductive carbonylation process or the process for making catalyst provided by the present invention. Some examples of suitable reactor types include stirred tank, continuous stirred tank, tower, plug flow reactor, bubble column, heated tube type reactor and tubular reactor. The process also may be practiced in a batchwise manner by contacting the low molecular weight alcohol, hydrogen and carbon monoxide with the present catalyst composition in an autoclave. Thus, in one embodiment, the reaction zone is selected from one of the foregoing reactor types. Embodiments exist of each such type.

The amount of catalyst used in the process can be measured in terms of the moles of cobalt, the moles of phosphine ligand and/or the molar ratio of phosphine ligand to cobalt (phosphine ligand:cobalt) per moles of feed alcohol. In one aspect, the cobalt-containing precursor is present in an amount such that the crude reductive carbonylation product comprises ranging from 0.001 moles to 50 moles of precursor cobalt equivalents per 100 moles of feed alcohol. Other examples of cobalt concentration include 0.001 moles to 10 moles of precursor cobalt equivalents per 100 moles of feed alcohol and 0.01 moles to 2 moles precursor cobalt equivalents per 100 moles of feed alcohol. In one aspect, the phosphine ligand is present in the crude reductive carbonylation product in an amount ranging from 0.005 moles to 5 moles of phosphine ligand per 100 moles of feed alcohol. Other examples of phosphine ligand concentration include 0.01 moles to 2 moles of phosphine ligand per 100 moles of feed alcohol and 0.01 moles to 0.8 moles of phosphine ligand per 100 moles of feed alcohol. For the measurement of the above ratios in a batch reaction can be determined based on the moles of catalyst charged per 100 moles of feed alcohol charged to the batch reactor. For a continuous reaction, the amounts can be determined based on the moles of catalyst fed per 100 moles of feed alcohol fed to the reactor over a given time period. The catalyst and the feed alcohol can be fed to the reactor together or separately.

The reductive carbonylation process can be carried out at any suitable temperature. In one example, temperature ranges from 100° C. to 250° C. In one embodiment, temperature ranges from 150° C. to 230° C. Temperature ranging from 170° C. to 210° C. has been found useful in some cases.

The reductive carbonylation process can be carried out any suitable pressure. In one embodiment, pressure ranges from 15 psig to 8700 psig. In other examples, the pressure ranges from 150 psig to 5800 psig, from 1000 psig to 4900 psig, from 3000 to 4500 psig or from 2000 to 4500 psig.

In one aspect, the reductive carbonylation process is carried out at a temperature ranging from 100° C. to 250° C. and a pressure of from 15 psig to 8700 psig. In another aspect, the reductive carbonylation process is carried out at a temperature ranging from 150° C. to 230° C. and a pressure of from 1000 psig to 4900 psig. In another aspect, the reductive carbonylation process is carried out at a temperature ranging from 150° C. to 230° C. and a pressure of from 2000 to 4500 psig. In another aspect, the reductive carbonylation process is carried out at a temperature ranging from 170° C. to 210° C. and a pressure of from 2000 to 3000 psig. In another aspect, the reductive carbonylation process is carried out at a temperature ranging from 170° C. to 200° C. and a pressure of from 2000 to 3000 psig.

In one aspect of the process of invention, the contacting of the hydrogen, carbon monoxide, and alcohol can occur in the presence of a solvent selected from alkanes and arenes having 6 to 20 carbon atoms, ketones having 5 to 20 carbon atoms, esters having 5 to 20 carbon atoms, ethers having 5 to 20 carbon atoms, and alkyl carbonate esters having from 3 to 20 carbon atoms. Some representative examples of the solvent include, but are not limited to, hexane, heptane, octane, decane, benzene, toluene, xylenes, methyl napththalenes, 3-methyl-2-butanone, methyl isobutyl ketone (also known as 4-methyl-2-pentanone), methyl isopropyl ketone, methyl propyl ketone, diisobutyl ketone, isobutylisobutyrate, ethyl acetate, n-butyl acetate, isobutylacetate, isopropylacetate, n-propyl acetate, diisopropylether, dibutylether, tertiary-amyl methyl ether, tertiary-butyl methyl ether, and mixtures thereof. In one aspect of our invention, the solvent can be selected from at least one of the group consisting of toluene, heptane, cyclohexane, ethylbenzene, diethyl ether, and 4-methylanisol.

The amount of solvent used is not critical to the subject invention. For example, the solvent can be present in an amount ranging from 5 vol % to 90 vol % based on the total volume of solvent and alcohol. In other examples, the solvent can be present in an amount ranging from 10 vol % to 80 vol %: 20 vol % to 60 vol %: or 30 vol % to 50 vol %, each based on the total volume of solvent and alcohol.

Listing of Non-Limiting Embodiments

The invention provides processes for making a catalyst composition. The processes comprises providing a liquid composition and combining the liquid composition and a promoter. The liquid composition comprises a product of contacting a cobalt-containing precursor with a phosphine ligand in the presence of a carrier liquid. The promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing. The phosphine ligand is of the general formula

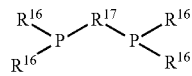

In the above formula, phosphorus atoms P are bridged by 2 or 3 atoms of $R^{17}$, and $R^{17}$ is selected from at least one of the group consisting of substituted or unsubstituted alkylene, cycloalkylene, arylene, and biarylene, each having up to 22 carbon atoms. A heteroatom optionally can substitute for one or more of the carbon atoms. The heteroatom is selected from at least one of the group consisting of nitrogen, oxygen, sulfur, and phosphorus. $R^{16}$ is selected from at least one of the group consisting of substituted or unsubstituted alkyl, alkoxy, cycloalkyl, aryl, and aryloxy, each having up to 20 carbon atoms.

The invention further provides catalyst compositions produced by a process comprising providing a liquid composition and combining the liquid composition and a promoter.

The liquid composition comprises a product of contacting a cobalt-containing precursor with a phosphine ligand in the presence of a carrier liquid. The promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing. The phosphine ligand is of the general formula

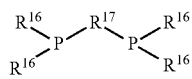

In the above formula, phosphorus atoms P are bridged by 2 or 3 atoms of $R^{17}$, and $R^{17}$ is selected from at least one of the group consisting of substituted or unsubstituted alkylene, cycloalkylene, arylene, and biarylene, each having up to 22 carbon atoms. A heteroatom optionally can substitute for one or more of the carbon atoms. The heteroatom is selected from at least one of the group consisting of nitrogen, oxygen, sulfur, and phosphorus. $R^{16}$ is selected from at least one of the group consisting of substituted or unsubstituted alkyl, alkoxy, cycloalkyl, aryl, and aryloxy, each having up to 20 carbon atoms.

The invention further provides embodiments of both the catalyst composition and the method of making a catalyst composition, including various embodiments having each of the features, ranges and combinations of features and ranges described in the paragraphs above, wherein the cobalt-containing precursor is selected from cobalt halides, cobalt carbonyls, and cobalt containing organic ligands. The invention further provides embodiments of both the catalyst composition and the method of making a catalyst composition, including various embodiments having each of the features, ranges and combinations of features and ranges described in the paragraphs above, wherein the cobalt-containing precursor is selected from cobalt iodide, dicobalt octacarbonyl, and tetracobalt dodecacarbonyl. The invention further provides embodiments of both the catalyst composition and the method of making a catalyst composition, including various embodiments having each of the features, ranges and combinations of features and ranges described in the paragraphs above, wherein the cobalt-containing precursor is selected from cobalt iodide and dicobalt octacarbonyl. The invention further provides embodiments of both the catalyst composition and the method of making a catalyst composition, including various embodiments having each of the features, ranges and combinations of features and ranges described in the paragraphs above, wherein the cobalt-containing precursor is cobalt iodide.

The invention further provides embodiments of both the catalyst composition and the method of making a catalyst composition, in which the cobalt-containing precursor is selected from cobalt halides, cobalt carbonyls and cobalt containing organic ligands and the iodine compound is selected from at least one of the group consisting of iodine, methyl iodide, lithium iodide, hydroiodic acid, sodium iodide.

The invention further provides embodiments of both the catalyst composition and the method of making a catalyst composition, including various embodiments having each of the features and combinations of features described in the paragraphs above, wherein the phosphine ligand and the cobalt-containing precursor are used in the process in amounts that provide a molar ratio of the phosphine ligand to precursor cobalt equivalents (phosphine ligand:precursor Co) that ranges from 0.01:1 to 2:1, from 0.025:1 to 2:1, from 0.025:1 to 0.5, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10 or from 2:1 to 1:5.

The invention further provides embodiments of both the catalyst composition and the method of making a catalyst composition, including various embodiments having each of the features, ranges and combinations of features and ranges described in the paragraphs above, wherein the molar ratio of the phosphine ligand to the promoter iodine equivalents (ligand:promoter iodine) used in making the catalyst ranges from 100:1 to 1:100, from 0.025:1 to 2:1, from 0.025:1 to 0.5, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10, from 2:1 to 1:5, from 10:1 to 1:50, from 5:1 to 1:10, from 0.025:1 to 2:1, from 0.025:1 to 0.5:1, from 0.025:1 to 1:1, from 0.025:1 to 1.5:1, from 0.1:1 to 1:1, from 0.1:1 to 0.1:1.5, from 1:1 to 2:1, from 10:1 to 1:50, from 2:1 to 1:10, from 1:1 to 1:10, from 3:1 to 1:10, or from 1:1 to 1:3.

The invention further provides embodiments of both the catalyst composition and the method of making a catalyst composition, including various embodiments having each of the features, ranges and combinations of features and ranges described in the paragraphs above, wherein the molar ratio of the promoter iodine equivalents to precursor cobalt equivalents (promoter iodine:precursor Co) ranges from 100:1 to 1:10, from 0.025:1 to 2:1, from 0.025:1 to 0.5:1, from 0.025:1 to 1:1, from 0.025:1 to 1.5:1, from 0.1:1 to 1:1, from 0.1:1 to 0.1:1.5, from 1:1 to 2:1, from 50:1 to 1:10, from 10:1 to 1:2, from 20:1 to 1:1, from 10:1 to 1:3, from 5:1 to 1:1, from 100:1 to 1:10, from 50:1 to 1:1, from 10:1 to 1:1, or from 3:1 to 1:1.

The invention further provides embodiments of both the catalyst composition and the method of making a catalyst composition, including various embodiments having each of the features, ranges and combinations of features and ranges described in the paragraphs above, wherein the phosphine ligand is of the general formula

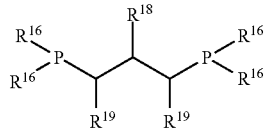

In the above formula $R^{18}$ is selected from at least one of the group consisting of a hydrogen radical and a hydrocarbon radical having up to 17 carbon atoms. The hydrocarbon radical can be substituted with at least one substituent selected from the group consisting of alkyl, alkoxy, cycloalkyl, aryl, aryloxy, dialkylphosphinomethyl, and diarylphosphinomethyl. $R^{19}$ is selected from at least one of the group consisting of hydrogen radical, substituted or unsubstituted alkyl, alkoxy, cycloalkyl, aryl, and aryloxy, each having up to 8 carbon atoms. Further, invention further provides embodiments of both the catalyst composition and the method of making a catalyst composition, as described in this paragraph, wherein $R^{16}$ is selected from at least one of the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy; $R^{18}$ is selected from at least one of the group consisting of hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butylphosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosphinomethyl, di-iso-butoxyphosphinomethyl, di-tert-butoxyphosphinomethyl diphenylphosphinomethyl, ditolylphosphinomethyl, and dixylylphosphinomethyl; and $R^{19}$ is a hydrogen radical.

The invention further provides embodiments of both the catalyst composition and the method of making a catalyst composition, including various embodiments having each of the features, ranges and combinations of features and ranges described in the paragraphs above, wherein the phosphine ligand is selected from at least one of the group consisting of 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino)propane; 2,4-bis(dicyclohexylphosphino)pentane; 1,2-bis(dimethylphosphino)ethane; 1,3-bis(dimethylphosphino)propane; 2,4-bis(dimethylphosphino)pentane; 1,2-bis(diisopropylphosphino)ethane; 1,3-bis(diisopropylphosphino)propane; 2,4-bis(diisopropylphosphino)pentane; 1,2-bis(di-tert-butylphosphino)ethane; 1,3-bis(di-tert-butylphosphino)propane; 2,4-bis(di-tert-butylphosphino)pentane; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; 1,3-bis(diphenylphosphino)cyclobutane; 1,2-bis(diphenylphosphino)cyclohexane; 1,2-bis(diphenylphosphino)cyclopentane; 1,2-bis(diphenylphosphino)cyclobutane; and/or 1,2-bis(diphenylphosphino)cyclopropane.

The invention further provides embodiments of both the catalyst composition and the method of making a catalyst composition, including various embodiments having each of the features, ranges and combinations of features and ranges described in the paragraphs above, wherein the phosphine ligand is 1,2-bis(diphenylphosphino)ethane; 1,2-bis(diphenylphosphino)benzene; 1,3-bis(diphenylphosphino)propane; and/or 1,1,1-tris(diphenylphosphinomethyl)ethane.

The invention further provides embodiments of both the catalyst composition and the method of making a catalyst composition, including various embodiments having each of the features, ranges and combinations of features and ranges described in the paragraphs above, wherein the cobalt-containing precursor comprises cobalt(II) iodide; the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphino-methyl)ethane; and the iodine compound is selected from at least one of the group consisting of iodine, methyl iodide, and lithium iodide.

The invention further provides embodiments of both the catalyst composition and the method of making a catalyst composition, including various embodiments having each of the features, ranges and combinations of features and ranges described in the paragraphs above, wherein The invention further provides embodiments of both the catalyst composition and the method of making a catalyst composition, including various embodiments having each of the features, ranges and combinations of features and ranges described in the paragraphs above, wherein the phosphine ligand is of the general formula

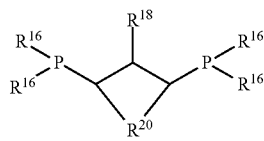

In this formula, $R^{20}$ can be a substituted or unsubstituted alkyl having up to 8 carbon atoms, forming a cycloalkyl group between the phosphorus atoms, $R^{18}$ is a hydrogen radical and $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy.

The invention further provides embodiments of both the catalyst composition and the method of making a catalyst composition, including various embodiments having each of the features, ranges and combinations of features and ranges described in the paragraphs above, wherein the compound that will form an alkyl iodide, hydroiodic acid, alkali metal iodides or elemental iodine under reductive carbonylation conditions comprises a compound selected from alkyl and aryl halides having from 1 to 12 carbon atoms. Optionally, the compound selected from alkyl and aryl halides having from 1 to 12 carbon atoms is selected from methyl iodide, ethyl iodide, 1-iodopropane, 2-iodobutane, 1-iodobutane, benzyl iodide, and combinations of two or more of the foregoing.

The invention further provides embodiments of both the catalyst composition and the method of making a catalyst composition, including various embodiments having each of the features, ranges and combinations of features and ranges described in the paragraphs above, wherein the compound that will form an alkyl iodide, hydroiodic acid, an alkali metal iodide or elemental iodine under reductive carbonylation conditions comprises a compound selected from alkyl halides having 1 to 6 carbon atoms.

The invention further provides embodiments of both the catalyst composition and the method of making a catalyst composition, including various embodiments having each of the features, ranges and combinations of features and ranges described in the paragraphs above, wherein the iodine compound is selected from lithium iodide, hydroiodic acid, sodium iodide, methyl iodide, ethyl iodide and elemental iodine. The invention further provides embodiments of both the catalyst composition and the method of making a catalyst composition, including various embodiments having each of the features, ranges and combinations of features and ranges described in the paragraphs above, wherein the iodine compound is selected from lithium iodide, methyl iodide and elemental iodine. The invention further provides embodiments of both the catalyst composition and the method of making a catalyst composition, including various embodiments having each of the features, ranges and combinations of features and ranges described in the paragraphs above, wherein the iodine compound is methyl iodide.

The invention further provides embodiments of both the catalyst composition and the method of making a catalyst composition, including various embodiments having each of the features, ranges and combinations of features and ranges described in the paragraphs above, wherein the cobalt precursor is selected from cobalt iodide, dicobalt octacarbonyl and tetracobalt dodecacarbonyl, the promoter is selected from lithium iodide, sodium iodide, hydroiodic acid, methyl iodide and elemental iodine, and the phosphine ligand is selected from 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino)propane; 2,4-bis(dicyclohexylphosphino)pentane; 1,2-bis(dimethylphosphino)ethane; 1,3-bis(dimethylphosphino)propane; 2,4-bis(dimethylphosphino)pentane; 1,2-bis(diisopropylphosphino)ethane; 1,3-bis(diisopropylphosphino)propane; 2,4-bis(diisopropylphosphino)pentane; 1,2-bis(di-tert-butylphosphino)ethane; 1,3-bis(di-tert-butylphosphino)propane; 2,4-bis(di-tert-butylphosphino)pentane; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; 1,3-bis(diphenylphosphino)cyclobutane; 1,2-bis(diphenylphosphino)cyclohexane; 1,2-bis(diphenylphosphino)cyclopentane; 1,2-bis(diphenylphosphino)cyclobutane; and/or 1,2-bis(diphenylphosphino)cyclopropane.

The invention further provides embodiments of both the catalyst composition and the method of making a catalyst composition, including various embodiments having each of the features, ranges and combinations of features and ranges described in the paragraphs above, wherein the cobalt precursor is selected from cobalt iodide and dicobalt octacarbonyl and tetracobalt dodecacarbonyl, the promoter is selected from methyl iodide, lithium iodide; hydroiodic acid and elemental iodine, and the phosphine ligand is selected from 1,3-bis(diphenylphosphino)propane, 1,2-bis(diphenylphosphino)ethane, 1,2-bis(diphenylphosphino)benzene, and 1,1,1-tris(diphenylphosphino-methyl)ethane.

The invention further provides embodiments of both the catalyst composition and the method of making a catalyst composition, including various embodiments having each of the features, ranges and combinations of features and ranges described in the paragraphs above, wherein the cobalt precursor is cobalt(II) iodide, the iodine compound is selected from at least one of the group consisting of iodine, methyl iodide, and lithium iodide, and the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphino-methyl)ethane.

The invention further provides embodiments of both the catalyst composition and the method of making a catalyst composition, including various embodiments having each of the features, ranges and combinations of features and ranges described in the paragraphs above, wherein the cobalt precursor is cobalt(II) iodide, the iodine compound is methyl iodide, and the phosphine ligand is 1,3-bis(diphenylphosphino)propane.

The invention provides processes for the preparation of a crude reductive carbonylation product. The process comprises contacting hydrogen, carbon monoxide, and a feed alcohol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The feed alcohol is selected from methanol, ethanol and n-propanol. The catalyst composition is made by a catalyst preparation process that comprises providing a liquid composition and combining the liquid composition and a promoter. The liquid composition comprises a product of contacting a cobalt-containing precursor with a phosphine ligand in the presence of a carrier liquid. The promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing. The phosphine ligand is of the general formula

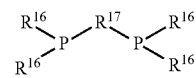

In the above formula, phosphorus atoms P are bridged by 2 or 3 atoms of $R^{17}$, and $R^{17}$ is selected from at least one of the group consisting of substituted or unsubstituted alkylene, cycloalkylene, arylene, and biarylene, each having up to 22 carbon atoms. A heteroatom optionally can substitute for one or more of the carbon atoms. The heteroatom is selected from at least one of the group consisting of nitrogen, oxygen, sulfur, and phosphorus. $R^{16}$ is selected from at least one of the group consisting of substituted or unsubstituted alkyl, alkoxy, cycloalkyl, aryl, and aryloxy, each having up to 20 carbon atoms.

The invention further provides embodiments of the processes for the preparation of a crude reductive carbonylation product having each of the features, ranges and combinations of features and ranges described in each of the paragraphs above with respect to the catalyst composition and the method of making a catalyst composition.

The invention further provides embodiments of the processes for the preparation of a crude reductive carbonylation product having each of the features, ranges and combinations of features and ranges described in each of the paragraphs above, wherein the feed alcohol is methanol.

The invention further provides embodiments of the processes for the preparation of a crude reductive carbonylation product having each of the features, ranges and combinations of features and ranges described in each of the paragraphs above, wherein the process is carried out at a temperature ranging from 100° C. to 250° C. and at a pressure ranging from 100 kPa (15 psig) to 60 MPa (8700 psig) and wherein the molar ratio of carbon monoxide to hydrogen, CO:H2, ranges from 10:1 to 1:10.

The invention further provides embodiments of the processes for the preparation of a crude reductive carbonylation product having each of the features, ranges and combinations of features and ranges described in each of the paragraphs above, wherein the amount of methyl iodide present in the crude reductive carbonylation product is less than 1 weight percent methyl iodide, less than 0.8 weight percent, less than 0.5 weight percent, less than 0.1 weight percent, less than 0.05 weight percent, less than 100 ppm, less than 50 ppm, less than 10 ppm, less than 100 ppb, less than 50 ppb, or less than 10 ppb of methyl iodide, based on the total weight of the crude reductive carbonylation product.

The invention further provides embodiments of the processes for the preparation of a crude reductive carbonylation product having each of the features, ranges and combinations of features and ranges described in each of the paragraphs above, wherein the molar ratio of carbon monoxide to hydrogen is from 50:1 to 1:50, from 10:1 to 1:10, from 5:1 to 1:5, from 3:1 to 1:3, from 2:1 to 1:2, from 10:1 to 1:1, from 5:1 to 1:1, from 2:1 to 1:1, from 2:1 to 1:5, from 1:1 to 1:5 or from 1:1 to 1:10.

The invention further provides embodiments of the processes for the preparation of a crude reductive carbonylation product having each of the features, ranges and combinations of features and ranges described in each of the paragraphs above wherein the cobalt-containing precursor is present in an amount such that the crude reductive carbonylation product comprises from 0.001 moles to 50 moles, from 0.001 moles to 10 moles or from 0.01 moles to 2 moles precursor cobalt equivalents per 100 moles of feed alcohol.

The invention further provides embodiments of the processes for the preparation of a crude reductive carbonylation product having each of the features, ranges and combinations of features and ranges described in each of the paragraphs above wherein the cobalt-containing precursor is present in an amount such that the crude reductive carbonylation product comprises phosphine ligand in an amount ranging from 0.005 moles to 5 moles from 0.01 moles to 2 moles, or from 0.01 moles to 0.8 moles of phosphine ligand per 100 moles of feed alcohol.

The invention further provides embodiments of the processes for the preparation of a crude reductive carbonylation product having each of the features, ranges and combinations of features and ranges described in each of the paragraphs above wherein temperature at which the process occurs is from 100° C. to 250° C., from 150° C. to 230° C., or from 170° C. to 210° C.

The invention further provides embodiments of the processes for the preparation of a crude reductive carbonylation product having each of the features, ranges and combinations of features and ranges described in each of the paragraphs above wherein pressure at which the process occurs is from 15 psig to 8700 psig, from 150 psig to 5800 psig, from 1000 psig to 4900 psig, from 3000 to 4500 psig or from 2000 to 4500 psig.

The invention further provides embodiments of the processes for the preparation of a crude reductive carbonylation product having each of the features, ranges and combinations of features and ranges described in each of the paragraphs above wherein pressure at which the process occurs is from 100° C. to 250° C. and from 15 psig to 8700 psig, from 150° C. to 230° C. and from 1000 psig to 4900 psig, from 150° C. to 230° C. and from 2000 to 4500 psig, from 170° C. to 210° C. and from 2000 to 3000 psig, or from 170° C. to 200° C. and from 2000 to 3000 psig.

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims. Unless otherwise indicated, all percentages are by weight.

EXAMPLES

Abbreviations $CoI_2$=cobalt(II) iodide

MeI=methyl iodide: LiI=lithium iodide: I2=iodine: DME=dimethyl ether:

dppm=1,1-bis(diphenylphosphino)methane; dppe=1,2-bis(diphenylphosphino)ethane; dppbenz=1,2-bis(diphenylphosphino)benzene; dppp=1,3-bis(diphenylphosphino)propane; dppb=1,4-bis(diphenylphosphino)butane; dpph=1,6-bis(diphenylphosphino)hexane; Ph-triphos=1,1,1-tris(diphenylphosphino-methyl)ethane; $PPh_3$=triphenylphosphine; (PPh2)3Me=1,1,1-tris(diphenylphosphino)methane; bipy=2,2'-bipyridine; P,N=2-(diphenylphosphino)-2'-(N,N-dimethylamino)biphenyl; phenan=1,10-phenanthroline STY=space time yield.

Selectivities

Selectivities are reported as selectivity to acetaldehyde equivalents, acetic acid equivalents, ethanol equivalents, and C4 equivalents relative to methanol carbonylated. Reported acetaldehyde equivalents include: Acetaldehyde, Paraldehyde, Acetaldehyde dimethyl acetal, Acetaldehyde methyl ethyl acetal, Acetaldehyde diethyl acetal. Reported acetic acid equivalents include: Acetic acid, Methyl acetate, and Ethyl acetate. Reported ethanol equivalents include all ethoxy containing products including: Ethanol, Acetaldehyde diethyl acetal, Acetaldehyde methyl ethyl acetal, Diethyl ether, Methyl ethyl ether, and Ethyl acetate. Reported C4 equivalents include: n-Butyl alcohol, Crotonaldehyde, n-Butyraldehyde, Butyraldehyde acetals, and Crotyl alcohol. A summary of commonly observed products and byproducts is provided in Table 1.

TABLE 1 commonly observed products incorporated into selectivity calculations for methanol reductive carbonylation

| Ethanol Equivalents | Acetaldehyde Equivalents | Acetic Acid Equivalents | C4 Equivalents |
|---|---|---|---|
| Ethanol | Acetaldehyde | Acetic acid | n-Butyl alcohol |
| Acetaldehyde diethyl acetal | Acetaldehyde dimethyl acetal | Methyl acetate | Crotonaldehyde |
| Acetaldehyde methyl ethyl acetal | Acetaldehyde methyl ethyl acetal | Ethyl acetate | n-Butyraldehyde |
| Diethyl ether | Acetaldehyde diethyl acetal | | Butyraldehyde acetals |
| Methyl ethyl ether | Paraldehyde | | Crotyl Alcohol |
| Ethyl acetate | | | |

Cobalt(II) iodide, phosphine ligands, iodide promoters, and methanol, were purchased and used without further processing The contents of the examples were analyzed by gas chromatography. Catalyst was not removed from the reaction product before analysis. Selectivities are reported based upon detection of the components listed in Table 1. The detection limit for methyl iodide (MeI) was 100 ppm. MeI listed as n/d indicates that no methyl iodide was detected.

Selectivities are reported as the sum of methanol carbonylated in the species divided by total amount of methanol carbonylated to a C2 as detailed in equations 1-4 below.

% Acetaldehyde Equivalents Selectivity=100*(moles Acetaldehyde+3*moles Paraldehyde+moles Acetaldehyde dimethyl acetal+moles Acetaldehyde methyl ethyl acetal+moles Acetaldehyde diethyl acetal)/moles Methanol Carbonylated % Acetic Acid Equivalents Selectivity=100*(moles Acetic acid+moles Methyl acetate+moles Ethyl acetate)/moles Methanol Carbonylated % Ethanol Equivalents Selectivity=100*(moles Ethanol+2*moles Acetaldehyde diethyl acetal+moles Acetaldehyde methyl ethyl acetal+2*moles Diethyl ether+moles Methyl ethyl ether+moles Ethyl acetate)/moles Methanol Carbonylated % C4 Equivalents Selectivity=100*(2*moles n-Butyl alcohol+2*moles Crotonaldehyde+2*moles n-Butyraldehyde+2*moles Butyraldehyde acetals+2*moles Crotyl alcohol)/moles Methanol Carbonylated.

The moles of Methanol Carbonylated were calculated as the difference between the initial amount of methanol and the recovered amount of free methanol. Methanol Conversion was calculated as the difference between the initial amount of methanol and the recovered amount of free methanol divided by the initial amount of methanol.

Yield of Carbonylated Products was calculated as the sum of the products derived from reductive carbonylation of methanol divided by the initial amount of methanol.

Space Time Yield (STY), for a methanol feed and with acetaldehyde equivalents as the desired product, was calculated as the moles of acetaldehyde equivalents produced per liter of initial reaction mixture per hours of reaction (moles per liter per hour, molL$^{-1}$ h$^{-1}$, Mh$^{-1}$).

Mole percent (Mole %) of methyl iodide (MeI) or dimethyl ether (DME) were calculated as the percentage of moles of species produced compared to the initial amount of methanol charged to the reactor.

Procedures

Except to the extent indicated otherwise for specific examples below, the reaction procedure was as follows. Samples were prepared by mixing CoI$_2$ (1.236 mmol) into 25 mL of methanol. Where applicable, ligand (1.236 mmol) was added and the resulting material was allowed to stand for at least 30 minutes (often longer, especially if visible solids did not form immediately) and promoter (where applicable) was then added (2.472 mmol). The resulting composition was then sealed until use in a reductive carbonylation reaction.

For examples identified as having an "incorrect mixing order" in Table 2, the procedure was modified as follows. Ligand and promoter were mixed together in 25 mL of methanol and allowed to stir overnight. The mixture was then added to the CoI$_2$ dissolved in 25 mL of methanol. Because the resulting samples included a total of 50 mL of methanol, in the "incorrect mixing order" examples, the amounts of CoI$_2$, ligand and promoter were doubled in those examples to result in the same concentrations in the methanol as the other examples.

For samples containing only CoI$_2$ and promoter, CoI$_2$ was mixed into 25. Once the CoI$_2$ is dissolved in the methanol, the promoter was then added. The resulting composition was then sealed until use in a reductive carbonylation reaction.

In each reductive carbonylation reaction, a 100-mL Hastelloy® C autoclave was charged with the composition, sealed and purged 3 times with N$_2$. The reactor was pressurized to 6.9 MPa (1000 psig) with 1:1 CO:H$_2$ and heated to 175° C. Upon reaching 175° C., the reactor was pressurized to a total pressure of 16.5 MPa (2400 psig) with 1:1 CO:H$_2$. After 30 minutes the reactor was cooled to 5° C. and the gas was vented. The contents were analyzed by gas chromatography.

Results of all runs are shown in Table 2 and discussed below. All example numbers beginning with "C" are comparative. Examples C1 through C4 used CoI$_2$ only without promoter or ligand. Examples C5 through C8 used CoI$_2$ and MeI promoter with no ligand. In Example C7 the promoter content was reduced by 50%. Examples C9 through C11 used CoI$_2$ and dppp ligand with no promoter.

Examples 1 to 10 used the inventive ligand dppp with CoI$_2$ and MeI promoter in the mixing order of the present invention while Examples C12-C14 were identical experiments except that the incorrect mixing order was used. As can be seen, using dppp and MeI in the inventive mixing order results in a marked increase in space-time yield as compared to experiments using the improper mixing order, as well as compared to experiments using CoI$_2$ alone (C1 to C4), CoI$_2$ and MeI only (C5 to C8), or CoI$_2$ and ligand only (C9 to C11).

Examples 11-13 and 14-15 demonstrate performance of dppp with promoter and CoI$_2$ in the inventive mixing order using lithium iodide (LiI) and elemental iodine (I2), respectively, as the promoter. The I2 concentration used in Examples 14 and 15 was reduced by 50% because I2 contains twice as many iodine atoms as MeI and LiI.

Examples 16-24 demonstrate performance of other ligands of the present invention using the inventive mixing order. These include dppe (Examples 16-19) and dppbenz (Examples 21-23), both of which have two phosphorus atoms bridged by 2 carbon atoms of R$^{17}$. For dppbenz, improved results were demonstrated by reducing the concentration of both ligand and promoter by 50% (Example 23). Performance was better than comparative examples C1-C11, including an experiment using promoter only with promoter concentration reduced by 50% (C7). Example 24 demonstrates performance using the inventive mixing order with the inventive ligand Ph-triphos, which, like dppp, has phosphorus atoms bridged by 3 carbon atoms of R$^{17}$ of the present invention.

Examples C15 through C24 demonstrate performance of other types of phosphine ligands in which the two phosphorus atoms are bridged by 6 carbon atoms of R$^{17}$ (dpph, C15 to C17), 4 carbon atoms of R$^{17}$ (dppb, C15 to C17), or one carbon atom of R$^{17}$ (dppm, C21 to C24). Unlike dppbenz (Example 23, discussed above), for dpph (see Example C17) nor dppm (see Example C24) improved to levels similar to the inventive ligands upon reducing the CoI$_2$ and MeI concentrations by 50%. Performance of dppm without promoter (Example C22) is also shown. Examples C25 to C30 show performance of a variety of other noninventive ligands.

Examples 25 to 31 show present data when manipulating certain reaction parameters. All of 25-31 are performed at reaction pressure of 4000 rather than 2400 psig, and 30 and 31 are further performed with a reaction temperature of 190° C. rather than 175° C.

TABLE 2

Reductive carbonylation of methanol to acetaldehyde equivalents; except where indicated (see notes at bottom of table), parameters were: 175° C.; 2400 psig; carbon monoxide to hydrogen ratio of 1:1 for 30 minutes with 0.2 mole % CoI2, 0.4 mole % promoter (if present) and 0.2 mole % ligand (if present). n/a = "not applicable," meaning component was not used.

| Ex | Promoter | Promoter Conc. (mole % relative to Methanol) | Ligand | Ligand Conc. (mole % relative to Methanol) | Methanol Conversion | Yield of Carbonylated Products | Acetaldehyde Selectivity | Ethanol Selectivity | Acetic Acid Selectivity | C4 Selectivity | STY (Mh$^{-1}$) | Mole % MeI in product | Mole % DME in product |
|---|---|---|---|---|---|---|---|---|---|---|---|---|---|
| C1 | n/a | n/a | n/a | n/a | 50% | 18% | 80% | 2% | 13% | 4% | 7 | n/d | 0.75% |
| C2 | n/a | n/a | n/a | n/a | 52% | 19% | 79% | 2% | 15% | 4% | 7 | n/d | 0.55% |
| C3 | n/a | n/a | n/a | n/a | 47% | 14% | 82% | 2% | 13% | 3% | 6 | n/d | 0.50% |
| C4 | n/a | n/a | n/a | n/a | 44% | 15% | 83% | 2% | 13% | 3% | 6 | n/d | 0.54% |
| C5 | MeI | 0.4% | n/a | n/a | 46% | 12% | 82% | 1% | 15% | 3% | 5 | 0.29% | 2.19% |
| C6 | MeI | 0.4% | n/a | n/a | 50% | 13% | 83% | 1% | 14% | 3% | 5 | 0.29% | 2.58% |
| C7 | MeI | 0.2% | n/a | n/a | 46% | 13% | 84% | 1% | 12% | 2% | 5 | n/d | 0.46% |
| C8 | MeI | 0.4% | n/a | n/a | 44% | 12% | 86% | 1% | 12% | 2% | 5 | n/d | 0.55% |
| C9 | n/a | n/a | dppp | 0.2% | 48% | 16% | 76% | 12% | 11% | 1% | 6 | 0.01% | 0.93% |
| C10 | n/a | n/a | dppp | 0.2% | 45% | 16% | 76% | 12% | 10% | 2% | 6 | 0.02% | 1.01% |
| C11 | n/a | n/a | dppp | 0.2% | 53% | 17% | 74% | 10% | 15% | 2% | 6 | n/d | 0.72% |
| *C12 | MeI | 0.4% | dppp | 0.2% | 54% | 15% | 83% | 1% | 15% | 2% | 6 | 0.02% | 0.99% |
| *C13 | MeI | 0.4% | dppp | 0.2% | 42% | 15% | 86% | 1% | 12% | 1% | 6 | 0.01% | 1.01% |
| *C14 | MeI | 0.2% | dppp | 0.2% | 43% | 17% | 84% | 3% | 13% | 1% | 7 | 0.01% | 0.35% |
| 1 | MeI | 0.4% | dppp | 0.2% | 69% | 27% | 78% | 4% | 16% | 3% | 11 | 0.03% | 2.45% |
| 2 | MeI | 0.4% | dppp | 0.2% | 61% | 22% | 82% | 6% | 11% | 2% | 9 | 0.04% | 3.16% |
| 3 | MeI | 0.4% | dppp | 0.2% | 58% | 19% | 84% | 6% | 9% | 1% | 8 | 0.03% | 2.70% |
| 4 | MeI | 0.4% | dppp | 0.2% | 69% | 26% | 77% | 5% | 16% | 2% | 10 | n/d | 2.88% |
| 5 | MeI | 0.4% | dppp | 0.2% | 70% | 27% | 77% | 4% | 17% | 3% | 10 | 0.04% | 3.57% |
| 6 | MeI | 0.6% | dppp | 0.3% | 68% | 26% | 77% | 4% | 17% | 1% | 10 | n/d | 2.82% |
| 7 | MeI | 0.4% | dppp | 0.2% | 59% | 20% | 80% | 5% | 14% | 1% | 8 | 0.04% | 2.61% |
| 8 | MeI | 0.4% | dppp | 0.2% | 74% | 22% | 78% | 4% | 14% | 1% | 9 | n/d | 2.86% |
| 9 | MeI | 0.4% | dppp | 0.2% | 62% | 24% | 78% | 8% | 11% | 4% | 9 | 0.01% | 3.15% |
| 10 | MeI | 0.4% | dppp | 0.2% | 62% | 23% | 78% | 8% | 11% | 3% | 9 | n/d | 2.85% |
| 11 | LiI | 0.4% | dppp | 0.2% | 60% | 21% | 76% | 6% | 17% | 1% | 8 | 0.03% | 0.77% |
| 12 | LiI | 0.4% | dppp | 0.2% | 57% | 22% | 77% | 6% | 17% | 1% | 8 | 0.04% | 0.94% |
| 13 | LiI | 0.4% | dppp | 0.2% | 58% | 20% | 74% | 7% | 17% | 2% | 7 | n/d | 0.66% |
| 14 | I2 | 0.2% | dppp | 0.2% | 71% | 26% | 75% | 2% | 17% | 5% | 10 | 0.11% | 2.16% |
| 15 | I2 | 0.2% | dppp | 0.2% | 69% | 26% | 76% | 2% | 18% | 5% | 10 | 0.13% | 2.33% |
| 16 | MeI | 0.4% | dppe | 0.2% | 44% | 15% | 84% | 1% | 14% | 1% | 6 | 0.01% | 2.58% |
| 17 | MeI | 0.4% | dppe | 0.2% | 66% | 22% | 79% | 4% | 15% | 2% | 9 | 0.16% | 3.42% |
| 18 | MeI | 0.4% | dppe | 0.2% | 74% | 19% | 75% | 5% | 18% | 2% | 7 | n/d | 2.23% |
| 19 | MeI | 0.4% | dppe | 0.2% | 68% | 22% | 76% | 5% | 17% | 2% | 8 | n/d | 3.06% |
| 20 | MeI | 0.2% | dppe | 0.1% | 63% | 23% | 79% | 3% | 15% | 3% | 9 | 0.10% | 1.65% |
| 21 | MeI | 0.4% | dppbenz | 0.2% | 54% | 14% | 70% | 10% | 20% | 0% | 5 | n/d | 4.37% |
| 22 | MeI | 0.4% | dppbenz | 0.2% | 70% | 19% | 74% | 7% | 18% | 2% | 7 | n/d | 2.13% |
| 23 | MeI | 0.2% | dppbenz | 0.1% | 65% | 23% | 77% | 5% | 15% | 2% | 9 | 0.23% | 2.29% |
| 24 | MeI | 0.4% | Ph-triphos | 0.2% | 69% | 24% | 79% | 2% | 17% | 3% | 9 | n/d | 1.51% |
| C15 | MeI | 0.4% | dpph | 0.2% | 25% | 10% | 93% | 1% | 5% | 1% | 5 | n/d | 0.66% |
| C16 | MeI | 0.4% | dpph | 0.2% | 50% | 19% | 83% | 1% | 15% | 1% | 8 | n/d | 0.64% |
| C17 | MeI | 0.2% | dpph | 0.1% | 47% | 17% | 82% | 2% | 15% | 2% | 7 | n/d | 0.46% |
| C18 | MeI | 0.4% | dppb | 0.2% | 39% | 15% | 84% | 1% | 14% | 1% | 6 | 0.01% | 1.46% |
| C19 | MeI | 0.4% | dppb | 0.2% | 47% | 17% | 81% | 1% | 16% | 2% | 7 | n/d | 0.43% |
| C20 | MeI | 0.2% | dppb | 0.1% | 52% | 18% | 80% | 2% | 16% | 3% | 7 | n/d | 0.40% |
| C21 | MeI | 0.4% | dppm | 0.2% | 48% | 15% | 84% | 1% | 14% | 2% | 6 | 0.11% | 1.91% |
| C22 | n/a | n/a | dppm | 0.2% | 42% | 14% | 77% | 16% | 7% | 0% | 5 | n/d | 0.96% |
| *C23 | MeI | 0.4% | dppm | 0.2% | 46% | 15% | 83% | 1% | 14% | 2% | 6 | 0.14% | 2.22% |
| C24 | MeI | 0.2% | dppm | 0.1% | 49% | 16% | 82% | 1% | 15% | 2% | 6 | n/d | 1.24% |
| C25 | MeI | 0.4% | P,N | 0.2% | 47% | 16% | 83% | 1% | 15% | 1% | 7 | 0.11% | 2.90% |
| C26 | MeI | 0.4% | (PPh2)3Me | 0.2% | 46% | 12% | 82% | 1% | 16% | 1% | 5 | n/d | 1.87% |
| C27 | MeI | 0.4% | bipy | 0.2% | 34% | 9% | 86% | 1% | 13% | 1% | 4 | 0.30% | 3.89% |
| C28 | MeI | 0.4% | phenan | 0.2% | 33% | 10% | 86% | 1% | 13% | 1% | 4 | 0.30% | 3.64% |
| C29 | MeI | 0.4% | PPh3 | 0.2% | 45% | 12% | 84% | 1% | 14% | 1% | 5 | 0.14% | 1.32% |
| C30 | MeI | 0.4% | PPh3 | 0.2% | 45% | 12% | 83% | 1% | 15% | 1% | 4 | 0.26% | 1.94% |
| **25 | MeI | 0.4% | dppp | 0.2% | 81% | 41% | 67% | 6% | 19% | 9% | 14 | n/d | 2.59% |
| **26 | MeI | 0.4% | dppp | 0.2% | 77% | 33% | 75% | 8% | 11% | 6% | 12 | 0.02% | 2.12% |
| **27 | MeI | 0.4% | dppp | 0.2% | 77% | 34% | 75% | 7% | 12% | 6% | 12 | 0.01% | 2.13% |
| **28 | MeI | 0.4% | dppp | 0.2% | 76% | 42% | 70% | 8% | 13% | 9% | 15 | n/d | 2.51% |
| **29 | MeI | 0.4% | dppp | 0.2% | 79% | 36% | 70% | 8% | 13% | 9% | 13 | n/d | 2.06% |
| ***30 | MeI | 0.4% | dppp | 0.2% | 80% | 39% | 71% | 7% | 14% | 8% | 14 | n/d | 2.58% |
| ***31 | MeI | 0.4% | dppp | 0.2% | 81% | 44% | 70% | 7% | 13% | 9% | 15 | n/d | 2.62% |

*Incorrect Mixing Order
**Reaction pressure 4000 psig
***Reaction temperature 190° C.

The invention has been described in detail with particular reference to preferred embodiments thereof, but it will be understood that variations and modifications can be effected within the spirit and scope of the invention.

What is claimed is:

1. A catalyst composition produced by a process comprising:
   (a) providing a liquid composition comprising a product of contacting a cobalt-containing precursor with a phosphine ligand in the presence of a carrier liquid;
   (b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing;
   wherein the phosphine ligand is selected from at least one of the group consisting of 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino)propane; 2,4-bis(dicyclohexylphosphino)pentane; 1,2-bis(dimethylphosphino)ethane; 1,3-bis(dimethylphosphino)propane; 2,4-bis(dimethylphosphino)pentane; 1,2-bis(diisopropylphosphino)ethane; 1,3-bis(diisopropylphosphino)propane; 2,4-bis(diisopropylphosphino)pentane; 1,2-bis(di-tert-butylphosphino)ethane; 1,3-bis(di-tert-butylphosphino)propane; 2,4-bis(di-tert-butylphosphino)pentane; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; 1,3-bis(diphenylphosphino)cyclobutane; 1,2-bis(diphenylphosphino)cyclohexane; 1,2-bis(diphenylphosphino)cyclopentane; 1,2-bis(diphenylphosphino)cyclobutane; and 1,2-bis(diphenylphosphino)cyclopropane.

2. The catalyst composition of claim 1, wherein the cobalt-containing precursor is selected from cobalt halides, cobalt carbonyls and cobalt containing organic ligands and the iodine compound is selected from at least one of the group consisting of iodine, methyl iodide, lithium iodide, hydroiodic acid, sodium iodide.

3. The catalyst composition of claim 1, wherein the phosphine ligand and the cobalt-containing precursor are used in the process in amounts that provide a molar ratio of the phosphine ligand to precursor cobalt equivalents (phosphine ligand:precursor Co) that ranges from 2:1 to 1:100.

4. The catalyst composition of claim 1, wherein the promoter and the cobalt-containing precursor are used in the process in amounts that provide a molar ratio of promoter iodine equivalents to precursor cobalt equivalents (promoter iodine:precursor Co) that ranges from 200:1 to 1:10.

5. The catalyst composition of claim 1, wherein the phosphine ligand and the promoter are used in the process in amounts that provide a molar ratio of the phosphine ligand to promoter iodine equivalents (phosphine ligand:promoter iodine) that ranges from 100:1 to 1:100.

6. The catalyst composition of claim 1, wherein the cobalt-containing precursor comprises cobalt(II) iodide; the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphino-methyl)ethane; and the iodine compound is selected from at least one of the group consisting of iodine, methyl iodide, and lithium iodide.

7. A process for the preparation of a crude reductive carbonylation product, the process comprising contacting hydrogen, carbon monoxide, and a feed alcohol in the presence of a catalyst composition to form the crude reductive carbonylation product, wherein the crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents, wherein the feed alcohol is selected from methanol, ethanol and n-propanol and wherein the catalyst composition is made by a catalyst preparation process comprising:
   a) providing a liquid composition comprising a product of contacting a cobalt-containing precursor with a phosphine ligand in the presence of a carrier liquid;
   (b) combining the liquid composition and a promoter, wherein the promoter comprises an iodine compound selected from alkyl iodides, hydroiodic acid, alkali metal iodides, elemental iodine, compounds that will form an alkyl iodide, hydroiodic acid, an alkali metal iodide or elemental iodine under reductive carbonylation conditions or combinations of two or more of the foregoing; and the phosphine ligand is selected from at least one of the group consisting of 1,2-bis(diphenylphosphino)ethane; 1,2-bis(diphenylphosphino)benzene; 1,3-bis(diphenylphosphino)propane; 2,4-bis(diphenylphosphino)pentane; 1,1,1-tris(diphenylphosphinomethyl)ethane; 1,1,1-tris(diethylphosphinomethyl)ethane; 1,2-bis(dicyclohexylphosphino)ethane; 1,3-bis(dicyclohexylphosphino)propane; 2,4-bis(dicyclohexylphosphino)pentane; 1,2-bis(dimethylphosphino)ethane; 1,3-bis(dimethylphosphino)propane; 2,4-bis(dimethylphosphino)pentane; 1,2-bis(diisopropylphosphino)ethane; 1,3-bis(diisopropylphosphino)propane; 2,4-bis(diisopropylphosphino)pentane; 1,2-bis(di-tert-butylphosphino)ethane; 1,3-bis(di-tert-butylphosphino)propane; 2,4-bis(di-tert-butylphosphino)pentane; 2,2'-bis(diphenylphosphino)-1,1,1-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; 1,3-bis(diphenylphosphino)cyclobutane; 1,2-bis(diphenylphosphino)cyclohexane; 1,2-bis(diphenylphosphino)cyclopentane; 1,2-bis(diphenylphosphino)cyclobutane; and 1,2-bis(diphenylphosphino)cyclopropane.

8. The process of claim 7, wherein the feed alcohol is methanol.

9. The process of claim 7, wherein the cobalt-containing precursor is selected from cobalt halides, cobalt carbonyls and cobalt containing organic ligands and the iodine compound is selected from at least one of the group consisting of iodine, methyl iodide, lithium iodide, hydroiodic acid, sodium iodide.

10. The process of claim 7, wherein the feed alcohol is methanol, the cobalt-containing precursor comprises cobalt(II) iodide, the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphinomethyl)ethane, and the iodine compound is selected from elemental iodine, methyl iodide, and lithium iodide.

11. The process of claim 7, wherein the phosphine ligand and the cobalt-containing precursor are used in the process in amounts that provide a molar ratio of the phosphine ligand to precursor cobalt equivalents (phosphine ligand:precursor Co) that ranges from 2:1 to 1:100.

12. The process of claim 7, wherein the promoter and the cobalt-containing precursor are used in the process in amounts that provide a molar ratio of promoter iodine equivalents to precursor cobalt equivalents (promoter iodine:precursor Co) that ranges from 200:1 to 1:10.

13. The process of claim 7, wherein the phosphine ligand and the promoter are used in the process in amounts that provide a molar ratio of the phosphine ligand to promoter iodine equivalents (phosphine ligand:promoter iodine) that ranges from 100:1 to 1:100.

14. The process of claim 7, wherein the process is carried out at a temperature ranging from 100° C. to 250° C. and at a pressure ranging from 100 kPa (15 psig) to 60 MPa (8700 psig) and wherein the molar ratio of carbon monoxide to hydrogen, CO:H2, ranges from 10:1 to 1:10.

15. A process for the preparation of a crude reductive carbonylation product comprising contacting hydrogen, carbon monoxide, and methanol in the presence of the catalyst composition of claim 1 to form the crude reductive carbonylation product comprising acetaldehyde equivalents in a higher mole percent than acetic acid equivalents or ethanol equivalents, each based on the total moles of the acetaldehyde equivalents, the acetic acid equivalents, and the ethanol equivalents.

16. The process of claim 7, wherein the feed alcohol is methanol, the cobalt precursor is cobalt(II) iodide, the iodine compound is selected from at least one of the group consisting of iodine, methyl iodide, and lithium iodide, and the phosphine ligand is selected from at least one of the group consisting of 1,3-bis(diphenylphosphino)propane, 1,2-bis(diphenylphosphino)ethane, 1,2-bis(diphenylphosphino)benzene, and 1,1,1-tris(diphenylphosphino-methyl)ethane.

17. A process for making a catalyst composition, comprising:
   a) providing a liquid composition comprising a product of contacting a cobalt-containing precursor with 1,3-bis(diphenylphosphino)propane in the presence of a carrier liquid;
   b) combining the liquid composition and a promoter, wherein the promoter comprises an iodine compound selected from alkyl iodides.

\* \* \* \* \*